United States Patent [19]

Osypka

[11] Patent Number: 4,466,690
[45] Date of Patent: Aug. 21, 1984

[54] CONNECTOR FOR THE CONDUCTORS OF IMPLANTED MEDICAL DEVICES

[76] Inventor: Peter Osypka, Basler Strasse 109, D-7889 Grenzach, Fed. Rep. of Germany

[21] Appl. No.: 389,888

[22] Filed: Jun. 18, 1982

[30] Foreign Application Priority Data

Jun. 24, 1981 [DE] Fed. Rep. of Germany ....... 3124707

[51] Int. Cl.³ .............................................. H01R 4/02
[52] U.S. Cl. ............................. 339/272 A; 339/256 S; 339/275 R
[58] Field of Search .............. 339/272, 218, 275, 256 S

[56] References Cited

U.S. PATENT DOCUMENTS

| | | | |
|---|---|---|---|
| 1,305,153 | 5/1919 | Nowosielski | 339/272 A |
| 1,437,687 | 12/1922 | Sherman | 339/272 A |
| 3,181,113 | 4/1965 | Esser | 339/272 R |
| 3,538,492 | 11/1970 | Genovese | 339/272 A |
| 3,718,887 | 2/1973 | Solomon et al. | 339/218 M |

FOREIGN PATENT DOCUMENTS

| | | | |
|---|---|---|---|
| 662149 | 12/1936 | Fed. Rep. of Germany | 339/272 A |
| 508848 | 5/1976 | U.S.S.R. | 339/272 A |

*Primary Examiner*—Joseph H. McGlynn
*Assistant Examiner*—David L. Pirlot
*Attorney, Agent, or Firm*—Peter K. Kontler

[57] ABSTRACT

A connector for connecting the broken ends of a helical conducting element has an outer sleeve of synthetic plastic material which is surrounded by an insulating coating. A pair of insulating tubular extensions having outer diameters smaller than the outer diameter of the insulating coating project from the latter in axial direction of the connector. The outer sleeve accommodates a compressible, electrically conductive helix having an inner diameter sufficiently large to receive the broken ends of the helical conducting element. The helix and helical conducting element have approximately the same pitch. The outer sleeve is provided with threaded holes which mesh with grub screws bearing upon the external surface of the helix. The insulating coating which surrounds the outer sleeve has openings which register with the holes in the outer sleeve to thereby permit the grub screws to be inserted in the holes. In operation, each of the broken ends of the helical conducting element is passed through one of the tubular extensions so that it penetrates the helix. The grub screws are rotated to compress the helix thereby causing the coils of the same to squeeze between the windings at the broken ends of the helical conducting element. As a result, a mechanical and electrical connection is formed between the broken ends. The tubular extensions serve to insulate the joint.

26 Claims, 2 Drawing Figures

CONNECTOR FOR THE CONDUCTORS OF IMPLANTED MEDICAL DEVICES

BACKGROUND OF THE INVENTION

The invention relates generally to a connector for electrically and mechanically joining the conductors of implanted medical devices.

More particularly, the invention relates to a connector for joining the ends of a broken lead of an implanted medical device. Such a connector may, for example, be used to join the ends of a broken conductor of an electrode for an implanted cardiac pacemaker.

Connectors for electrically and mechanically joining the sections of broken electrodes for implanted cardiac pacemakers are known. One type of connector includes a form of screw joint which is composed of metal and has a pair of set screws or grub screws. The entire metallic screw joint is insulated and protected by a coating of synthetic plastic material. Another type of connector includes a metallic tube and the broken ends of an electrode are introduced into the tube from opposite sides of the latter. The tube is then compressed with the help of pliers.

Electrodes for cardiac pacemakers generally have helical conductors. When broken ends of such conductors are joined by connectors of the type described above, the conductors are deformed and stressed in such a manner by the grub screws or pliers that a new break may occur.

OBJECTS AND SUMMARY OF THE INVENTION

It is an object of the invention to provide a connector for the conductors of implanted medical devices which greatly reduces the likelihood that the conductors will fracture.

Another object of the invention is to provide a connector for the conductors of implanted medical devices which is relatively inexpensive yet enables good electrical and mechanical connections between the conductors to be established.

An additional object of the invention is to provide a connector of the type outlined above which makes it possible to establish firm mechanical and electrical connections between broken sections of an electrode for an implanted cardiac pacemaker with little danger of a new fracture.

The preceding objects, as well as others which will become apparent as the description proceeds, are achieved by the invention.

One aspect of the invention resides in a connector for joining the conductors of implanted medical devices, particularly broken sections of an electrode for an implanted cardiac pacemaker. The connector comprises an outer tubular member or sleeve as well as a deformable inner tubular member or sleeve which is accommodated in the outer sleeve and is designed to receive and clamp the end portions of a pair of conductors to be joined. At least one clamping member, and preferably a plurality of clamping members, is provided in the outer sleeve for deforming the inner sleeve so as to cause the same to clamp the end portions of the conductors.

The outer sleeve may include a pair of discrete, aligned tubular portions or may be of one piece. Furthermore, the outer sleeve may be provided with an insulating coating of an essentially inert synthetic plastic material or the like. Preferably, the outer sleeve is coated with silicone rubber.

According to a preferred embodiment of the invention, the outer sleeve consists essentially of a synthetic plastic material and the inner sleeve is electrically conductive.

In the connector of the invention, the forces exerted by the clamping members may be transmitted to the conductors relatively gently via the deformable inner sleeve so that the danger of fracture is eliminated or at least greatly reduced. Moreover, it is possible for the outer sleeve to consist essentially of a synthetic plastic material due to the fact that the deformable sleeve which performs the actual clamping function is located within the outer sleeve and is itself capable of establishing an electrical connection between the conductors. This enables the cost of the outer sleeve to be reduced and also permits this to provide an additional insulating effect. Furthermore, it becomes possible for the connector to have a certain degree of flexibility.

The outer sleeve may be internally threaded and the clamping members may be in the form of set screws or grub screws which mate with the internal threads of the outer sleeve and bear against the external surface of the deformable inner sleeve. It is particularly advantageous for the screws to be countersunk or to be otherwise arranged so as to be located inwardly of the external surface of the outer sleeve.

According to a particularly advantageous embodiment of the invention, the deformable inner sleeve is constituted by at least one metallic helix. The inner diameter of the helix in its undeformed condition is at least equal to the outer diameters of the conductors to be joined. A metallic helix can provide a good distribution of the clamping forces applied by the screws over the conductors. Moreover, the use of a metallic helix makes it possible for the inner sleeve and the conductors to be locked to one another. In this regard, it was mentioned previously that electrodes for cardiac pacemakers generally have helical conductors. When broken ends of such a helical conductor are to be joined, the use of a helical inner sleeve enables the shapes of the sleeve and the conductor to be matched.

It is especially favorable and economical for the inner sleeve to be constituted by a metallic helix which is of one piece and receives both of the conductors to be joined.

In the case of helical conductors, the neighboring windings define recesses with one another. When broken ends of such a conductor, or two such conductors, are to be joined, the inner sleeve may be in the form of a helix which is designed in such a manner that, in the deformed condition of the helix, that is, the condition of use of the helix, at least some of the coils of the helix are at least partly received in the recesses. This virtually automatically results in the locking effect mentioned earlier when the helix is pressed against the conductors.

When an inner sleeve in the form of a helix is used to join broken ends of a helical conductor or to join a pair of helical conductors, it is advantageous for the pitch of the helix to approximate that of the conductors. It is also of advantage for the coils of the helix in the deformed condition of the latter to be parallel to the windings of the conductors.

As indicated previously, the outer sleeve may be of one piece and may be composed essentially of a synthetic plastic material.

The connector may include a section having relatively large outer dimensions or a relatively large outer diameter as well as a pair of tubular extensions having smaller outer dimensions or a smaller outer diameter than this section. The large section of the connector, which is advantageously located centrally of the connector, accommodates the inner and outer sleeves. The tubular extensions project from opposite sides of the large section of the connector and are aligned with one another. These extensions are composed of an insulating material and the conductors to be joined pass through the extensions to the inner sleeve of the connector.

When broken ends of a conductor are to be joined, it may be necessary or advisable to remove the insulation in the regions of these ends. The extensions make it possible to provide a good insulating bridge across the break or, in other words, to provide a good transition in insulating effect from the insulated portions of the conductor to the broken ends. The extensions are capable of forming a seal with the insulation remaining on the conductor and accordingly of insulating the entire area of the break.

As mentioned earlier, the outer sleeve may be provided with an insulating coating. The extensions may be of one piece with such a coating.

In order to insure that a pair of conductors to be joined, or the broken ends of a conductor, project into the connector for a predetermined distance, the connector may be provided with a stop or abutment. The stop is advantageously metallic and is favorably located at the center of the connector.

It is of particular advantage for the stop to be in the form of a pin which traverses the inner sleeve and fixes the same against axial displacement. The pin then has a dual function, namely, that of serving as a stop for the conductors and that of serving as a retainer for the inner sleeve. The pin is preferably composed of stainless steel.

It is particularly simple to pass the pin through the inner sleeve when the latter is in the form of a helix since the pin may extend between the coils of the helix. Here, the helix may be securely fixed against axial displacement by locating the pin in the region of the connector having the largest dimensions or diameter.

The novel features which are considered as characteristic of the invention are set forth in particular in the appended claims. The improved connector itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
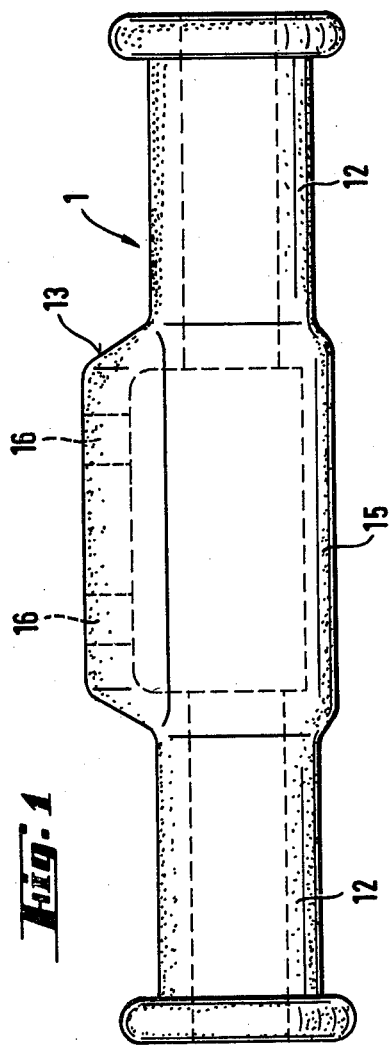
FIG. 1 is a side view of a connector according to the invention.
Figure 2:
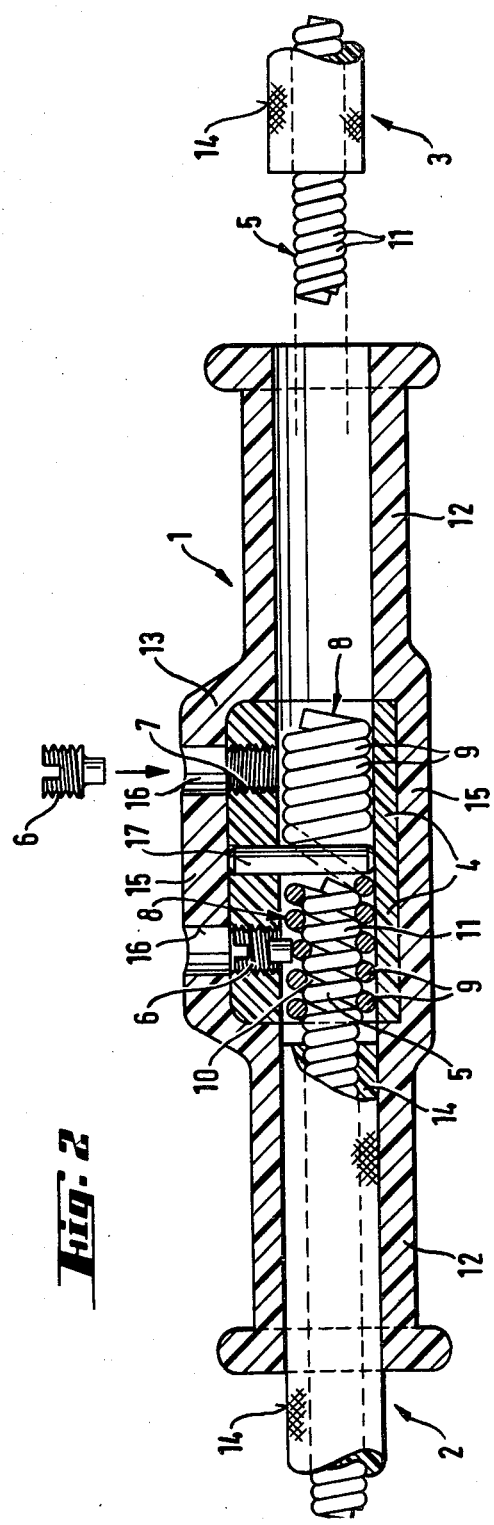
FIG. 2 is a longitudinal cross-sectional view through the connector of FIG. 1 illustrating the joining of the broken ends of a conductor constituting part of an electrode for an implanted cardiac pacemaker.

FIGS. 1 and 2 illustrate a connector 1 according to the invention. In the present case, the connector 1 functions to provide an electrical and mechanical joint between the broken ends 2 and 3 of an electrical conductor although it will be understood that the connector 1 could equally well be used to join the conductors of two different devices. The conductor having the broken ends 2 and 3 is here assumed to form part of an electrode for an implanted cardiac pacemaker. The conductor is composed of a helical wire 5 surrounded by insulation 14. It will be observed that the wire 5 is exposed in the region of the break.

The connector 1 has an outer sleeve comprising a pair of aligned, tubular sections 4 which are connected to one another. Although the tubular sections 4 may be discrete, they are here illustrated as being of one piece with each other. Accordingly, the following description will simply make reference to the outer sleeve 4 or the sleeve 4 rather than the tubular sections 4.

The outer sleeve 4 is composed of a synthetic plastic material and accommodates a deformable inner sleeve 8 which will be described more fully below. The inner sleeve 8 is sufficiently large to accommodate the helical wire of the conductor 5,14, that is, the inner diameter of the inner sleeve 8 is at least equal to the outer diameter of the helical wire 5. The exposed portion of the helical wire 5 at the end 2 of the conductor 5,14 is introduced into one side of the inner sleeve 8 while the exposed portion of the helical wire 5 at the end 3 of the conductor 5, 14 is introduced into the opposite side of the inner sleeve 8.

The outer sleeve 4 carries clamping members for compressing the inner sleeve 8 so as to cause the same to clamp the exposed portions of the helical wire 5. The clamping members are here in the form of set screws or grub screws 6. The outer sleeve 4 is provided with internal threads 7 which mesh with external threads on the screws 6. As illustrated, the screws 6 are preferably countersunk or otherwise arranged so as to be located inwardly of the external surface of the outer sleeve 4. The screws 6 bear against the external surface of the inner sleeve 8.

The inner sleeve 8 is here in the form of a metallic helix having coils 9. The inner diameter of the helix 8 before compression is at least equal to the outer diameter of the helical wire 5 of the conductor 5,14. Although the helix 8 may include a pair of discrete sections, it is here of one piece.

The left-hand side of FIG. 2 shows the helix 8 after it has been compressed by one or more of the screws 6 so as to clamp the end 2 of the conductor 5,14. It will be observed that the windings 11 of the helical wire 5 are forced apart as a result of the compressive forces exerted by the screw or screws 6. In this regard, the extended helical wire 5 at the end 2 may be compared with the unextended helical wire 5 at the end 3 on the right-hand side of FIG. 2. Neighboring ones of the windings 11 of the helical wire 5 define shallow grooves in the unextended condition of the helical wire 5. When the helical wire 5 is extended as on the left-hand side of FIG. 2, at least portions of the grooves expand to define larger recesses 10. The helix 8 is designed and arranged in such a manner that at least some of the coils 9 thereof are at least partly accommodated in the recesses 10. Thus, the helix 8 and the helical wire 5 are interengaged and a locking effect is achieved in the axial direction of the connector 1 under the influence of the screws 6. If both of the ends 2 and 3 are clamped in this manner, current can again flow in the conductor 5,14 via the metallic helix 8. In addition to the electrical connection which is established between the ends 2 and 3 by means of the helix 8, a secure mechanical connection including a locking effect is achieved.

The pitch of the helix 8 approximates that of the helical wire 5. Furthermore, as illustrated on the left-hand side of FIG. 2, the coils 9 of the compressed helix 8 are parallel to the windings 11 of the extended helical wire 5.

The outer sleeve 4 is provided with an insulating coating 15 of an inert synthetic plastic material. By way of example, the coating 15 may be composed of silicone rubber. The coating 15 is provided with openings 16 for inserting the screws 6 into the outer sleeve 4. The openings 16 are sealed with an appropriate substance such as, for instance, a silicone adhesive or the like, once the screws 6 have been screwed into the outer sleeve 4 so as to cause the helix 8 to clamp the ends 2 and 3 of the conductor 5,14.

The helix 8, the outer sleeve 4 and the coating 15 together constitute a section 13 of the connector 1 which is advantageously centrally positioned with respect to the latter. A pair of tubular extensions 12 having a smaller outer diameter than the section 13 project axially from opposite sides of the same. The tubular extensions 12, which are in axial alignment with one another, are composed of an insulating material. The ends 2 and 3 of the conductor 5,14 extend to the helix 8 via the respective tubular extensions 12. The inner diameters of the tubular extensions 12 are sufficiently large to accommodate the insulation 14 of the conductor 5,14 and a portion of the insulation 14 is received in each of the tubular extensions 12. In this manner, a good seal as well as a good insulating effect may be achieved in the region of the joint. The tubular extensions 12 are advantageously of one piece with the insulating coating 15 on the outer sleeve 4. The enlarged portions at the outer ends of the tubular extensions 12 permit application of a ligature.

A stop or abutment is provided at the middle of the outer sleeve 4. In the illustrated embodiment, the stop is in the form of a metallic pin 17 which extends transversely of the connector 1. Advantageously, the pin 17 is composed of stainless steel. The pin 17 traverses the helix 8 and it will be observed that the pin 17 is located between two of the coils 9 thereof. The pin 17 has two functions. On the one hand, the pin 17 insures that the ends 2 and 3 of the conductor 5,14 penetrate into the outer sleeve 4 by about the same distance. On the other hand, the pin 17 fixes the helix 8 against axial displacement.

In summary, the connector 1 is economical to manufacture and easy to handle. Moreover, the connector 1 enables the ends 2 and 3 of the conductor 5,14 to be securely yet carefully or gently connected to one another so that the danger of another fracture is eliminated or at least greatly reduced. This is due to the fact that the clamping force is exerted on the ends 2 and 3 of the conductor 5,14 via the helix 8 rather than directly by the screws 6. In addition, the helix 8 which serves to mechanically connect the ends 2 and 3 simultaneously serves to establish an electrical connection between the same so that the outer sleeve 4 may be composed of a synthetic plastic material. The cost of the connector 1 may be lowered by making the outer sleeve 4 of a synthetic plastic material since this is cheaper than metal.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A connector for joining the conductors of implanted medical devices, particularly the ends of broken conducting elements, comprising:
    (a) an outer tubular member;
    (b) a deformable inner tubular member accommodated in said outer member and designed to receive and clamp the end portions of a pair of conductors to be joined, said inner member including a helix; and
    (c) at least one clamping member in said outer member for deforming said helix so as to cause said helix to clamp the end portions of the conductors, the end portion of at least one of the pair of conductors to be joined being helical, and neighboring windings of such end portion cooperating to define recesses, said helix receiving the helical end portion and being arranged such that at least some coils of said helix are at least partly accommodated in said recesses subsequent to deformation of said helix.

2. A connector according to claim 1, comprising a plurality of clamping members in said outer member for deforming said inner member.

3. A connector according to claim 1, wherein said outer member comprises a pair of discrete, aligned tubular portions.

4. A connector according to claim 1, wherein said helix is metallic.

5. A connector according to claim 1, wherein said helix is of one piece and receives the end portions of both of the conductors to be joined.

6. A connector according to claim 1, wherein the conductors to be joined constitute two sections of a broken electrode for an implanted cardiac pacemaker.

7. A connector according to claim 1, wherein said inner member is electrically conductive.

8. A connector according to claim 7, wherein said outer member is composed essentially of a synthetic plastic material.

9. A connector according to claim 1, comprising an insulating coating on said outer member.

10. A connector according to claim 9, wherein said coating is composed essentially of an inert synthetic plastic material.

11. A connector according to claim 9, wherein said coating is composed essentially of silicone rubber.

12. A connector according to claim 1, wherein said clamping member comprises a screw which is threaded into said outer member and bears against the external surface of said inner member.

13. A connector according to claim 12, wherein said screw is located inwardly of the external surface of said outer member.

14. A connector according to claim 12, wherein said screw is a grub screw.

15. A connector according to claim 1, wherein said outer member is of one piece.

16. A connector according to claim 15, wherein said outer member is composed essentially of a synthetic plastic material.

17. A connector according to claim 1, wherein said outer and inner members are located in a section having a first outer dimension; and further comprising a pair of aligned insulating tubular extensions extending from opposite ends of said section and having a second outer dimension smaller than said first dimension, the end portions of the conductors to be joined passing through the respective extensions to said section.

18. A connector according to claim 17, wherein said section is substantially centrally located.

19. A connector according to claim 17, comprising an insulating coating on said outer member; and wherein said extensions are of one piece with said coating.

20. A connector according to claim 1, comprising an abutment in said inner member for positioning the end portions of the conductors to be joined.

21. A connector according to claim 20, wherein said abutment is substantially centrally located.

22. A connector according to claim 20, wherein said abutment comprises a pin which traverses said inner member and fixes the same against axial displacement.

23. A connector according to claim 20, wherein said abutment is metallic.

24. A connector according to claim 23, wherein said abutment is composed essentially of stainless steel.

25. A connector for joining the conductors of implanted medical devices, particularly the ends of broken conducting elements, comprising:
   (a) an outer tubular member;
   (b) a deformable inner tubular member accommodated in said outer member and designed to receive and clamp the end portions of a pair of conductors to be joined, said inner member including a helix; and
   (c) at least one clamping member in said outer member for deforming said helix so as to cause said helix to clamp the end portions of the conductors, the end portion of at least one of the pair of conductors to be joined being helical, and said helix receiving such end portion and having a pitch of the latter.

26. A connector for joining the conductors of implanted medical devices, particularly the ends of broken conducting elements, comprising:
   (a) an outer tubular member;
   (b) a deformable inner tubular member accommodated in said outer member and designed to receive and clamp the end portions of a pair of conductors to be joined, said inner member including a helix; and
   (c) at least one clamping member in said outer member for deforming said helix so as to cause said helix to clamp the end portions of the conductors, the end portion of at least one of the pair of conductors to be joined being helical, and said helix receiving such end portion and being arranged so that the coils thereof are substantially parallel to the windings of the helical end portion subsequent to deformation of said helix.

* * * * *